United States Patent [19]

De Luca et al.

[11] Patent Number: 4,551,471
[45] Date of Patent: Nov. 5, 1985

[54] USE OF 3-INDOLEPYRUVIC ACID FOR INCREASING SEROTONIN

[75] Inventors: Giovanna De Luca; Giovanni Di Stazio; Vincenzo Politi; Mario Materazzi, all of Rome, Italy

[73] Assignee: Polifarma S.p.A., Rome, Italy

[21] Appl. No.: 540,051

[22] Filed: Oct. 7, 1983

[30] Foreign Application Priority Data

Oct. 11, 1982 [IT] Italy .................. 49251 A/82

[51] Int. Cl.⁴ ................... A61K 31/405; C07D 209/20
[52] U.S. Cl. ..................................... 514/419; 548/494
[58] Field of Search .................. 424/277; 548/494; 514/419

[56] References Cited

PUBLICATIONS

Richards, J. Nutrition, vol. 102, pp. 1547-1550 (1972).
Haavaldsen, Biochemical Journal, 92, p. 23 (1964).
Truzhnikova et al., C.A., 75, 138075h (1971).
Grigor'ev et al., C.A., 75, 46021j (1971).
Akabori et al., C.A. 13146c (1960).

*Primary Examiner*—Richard L. Raymond
*Assistant Examiner*—D. B. Springer
*Attorney, Agent, or Firm*—Cushman, Darby & Cushman

[57] ABSTRACT

The process for the biosynthesis of 3-indolpyruvic acid involves the reaction of tryptophan with purified enzyme aspartate aminotransferase obtained from the mytochondria of slaughterhouse animals. When administered orally in rats, 3-indolpyruvic acid leads to a considerable increase in cerebral serotonin levels, and so may be used in all the pathological conditions of the central nervous system involving deficiencies of this neurotransmitter, such as depressions, insomnia, lack of appetite, neuroendocrin imbalances, etc.

4 Claims, No Drawings

USE OF 3-INDOLEPYRUVIC ACID FOR INCREASING SEROTONIN

FIELD OF THE INVENTION

The present invention relates to a new enzymatic process for the preparation of 3-indolpyruvic acid from tryptophan and α-ketoglutarate.

The invention also relates to the pharmaceutical applications of 3-indolpyruvic acid and its pharmaceutically acceptable esters and salts in the treatment of diseases of the central nervous system arising from the lack of cerebral serotonin, as well as pharmaceutical compositions containing 3-indolpyruvic acid, its esters, and salts as active ingredients.

BACKGROUND OF THE INVENTION 3-indolpyruvic acid has the following formula;

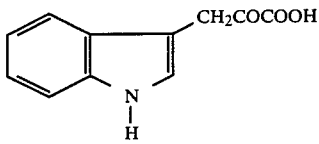

and is a ketoacid widely known in the literature since it is present in large quantities in plants and seeds, where it seems to be a growth enhancing agent.

In Japanese Pat. No. 4274 (28 May 1959), the acid is described as an intermediate product in the preparation of tryptophan from 3-indolacetic acid.

It was observed in 1964 that the ketoacid is a normal metabolite of mammalian central nervous systems (J. Biochem., 92, 23P), while subsequent work by Russian researchers showed that the ketoacid can favourably replace tryptophan as a growth enhancer for chickens. There are no reports that 3-indolpyruvic acid has ever been used for therapeutic purposes.

According to the present invention, it has recently been discovered that the ketoacid 3-indolpyruvic acid, administered orally to Sprague Dawley rats, is capable of considerably increasing cerebral serotonin levels, while leaving the cerebral concentrations of the other neurotransmitters practically unaltered, thus returning a pathologically unbalanced system to equilibrium.

Insufficient serotonin at the level of the central nervous system has often been related to the appearance of striking pathological phenomena, such as endogenous depressions, headaches, sleep and appetite disturbances, neuroendocrine imbalances, etc. .Since serotonin cannot cross the hematoencephalic barrier, and so cannot be administered as a drug, previous techniques involved the administration of its precursors, in order to increase cerebral levels.

L-tryptophan has been used in the Anglo-Saxon world for many years to treat insomnia and depressions, more recently, France and Italy have approved the use of 5-hydroxytryptophan to treat depressions and all other pathology related to the lack of cerebral serotonin.

Tryptophan, however, presents striking problems as a precursor of cerebral serotonin, since it is to a great degree degraded at the hepatic level by tryptophan pyrrolase toward the quinurenin cycle, itsis captured by the plasma proteins giving rise to unpredictable levels of the free aminoacid, and finally it competes with all the other neutral aminoacids for passage through the hematoencephalic barrier, all of which makes it practically impossible to predict its pharmacological effects.

5-hydroxytryptophan, in turn, also competes with the carrier which transports neutral aminoacids into the central nervous system, and may furthermore be decarboxylated to serotonin by catecholaminergic neurons as well, giving rise to possible imbalances in these neurotransmitter pathways also through the formation of false transmitters.

3-Indolpyruvic acid, on the other hand, is not degraded by tryptophan pyrrolase to such a degree, does not compete with the aminoacids for entrance to the central nervous system, and is first transformed to tryptophan, and then to serotonin, only by serotoninergic neurons, which have the enzyme tryptophan hydroxylase. Therefore the ketoacid may be seen as the most advantageous precursor for the biosynthesis of cerebral serotonin. Other considerations of a biochemical nature also lead to the preferred use of ketoacids to antagonize the increase in ammonia resulting from conditions of cellular distress. In fact, if the serotonin insufficiency is due to chronic deficiency of the precursor, it may be predicted that the use of aminoacids will have little effect, while the use of ketoacids would seem more rational since they can restore adequate precursor levels.

With regard to toxicity, there seem to be no problems for therapeutic levels, since administration of 500 mg in a woman caused no undesired effects (J. Nutr. 102, 1547 (1972)).

SUMMARY OF THE INVENTION

Therefore the present invention involves the use of 3-indolpyruvic acid and its pharmaceutically compatible salts in therapy, for the treatment of pathological conditions which can be related to deficiency of cerebral serotonin, such as depressions, headaches, lack of appetite, sleep and neuroendocrine disturbances, etc.

The invention also involves a new industrially applicable process for the enzymatic synthesis of 3-indolpyruvic acid starting from L-tryptophan, using the enzyme aspartate aminotransferase obtained from the mytochondria of animal organs. For reasons of accessibility, slaughterhouse animals such as pigs, cattle, oxen, etc. are preferred as the source of organs rich in mytochondria, such as heart, kidney, liver, etc.

The enzyme aspartate aminotransferase is a known product, and the techniques for extracting it from mytochondria from animal organs are well known.

The enzyme is purified to electrophoretic homogeneity using known methods (see Methods in Enzymology) and is used in this form in the enzymatic reaction with L-tryptophan.

The process according to the invention involves the operation of reacting L-tryptophan and α-ketoglutarate in the presence of both the enzyme aspartate aminotransferase and the coenzyme pyridoxalphosphate or pyridoxamine phosphate, in aqueous solution at a pH between 7 and 8 and at a temperature around 37° C., followed by separating the product 3-indolpyruvic acid from the reaction mixture and recycling the unreacted starting materials to the enzymatic reaction, as well as the enzyme.

The present process in therefore highly efficient for production on an industrial scale, since it is possible to recover and recycle the products which participated in the reaction.

DETAILED DESCRIPTION OF THE INVENTION

An example of the preparation of 3-indolpyruvic acid according to the present invention on is described below.

EXAMPLE 1

Preparation of 3-Indolpyruvic acid

The enzyme aspartate aminotransferase from pig heart mytochondria is purified as described above. An aliquot of enzyme equivalent to 2–4 mg of protein, is incubated at 37° C. in 100 ml of 0.1M TRIS-HCl buffer at pH 7,8. The resulting mixture is treated with 200 mg of L-tryptophan, 45 mg of α-ketoblutarate and 2,5 mg of pyridoxalphosphate. The pyridoxalphosphate may be replaced by an equivalent quantity of pyridoxamine phosphate.

After 4 hours of incubation, the mixture is filtered through Amicon YM-10 membrane, and the enzyme is recovered and recycled.

The ultrafiltrate is extracted with petroleum ether, enriching the organic phase with indolpyruvate.

The aqueous phase is evaporated to remove solvent residues, and is then recycled.

The organic phase is brought to dryness and taken up in methanol.

The crude products is placed on a semi-preparative C-18 column (0,8×30 CM, Waters company) and eluted with a water-alcohol mixture, thus separating the indolpyruvate from the impurities present.

EXAMPLE 2

In Vivo Pharmacological Studies

Twenty Sprague-Dawley male rats were divided into four groups of five animals each. Another five animals received no treatment, and acted as controls.

The four treated groups received 10 mg/kg of indolpyruvate orally; each group was sacrificed in turn after 30, 60, 75 and 90 minutes.

Plasma levels were determined for all animals and compared with those of the non-treated control animals (time 0).

Determinations of plasma levels

Blood samples (4 ml) from the sacrificed animals were treated with 0,4 ml of 10% EDTA and 0,1 ml of 20% vitamin C. The resulting mixture was centrifuged at 4000 revolutions per minute at 5° C. for 10 minutes. 0,7 ml of plasma were treated with 0,025 ml of 20% vitamin C and 0,3 ml of 12% trichloroacitic acid. The mixture was left at 5° C. for 20 minutes, and then centrifuged at 11,000 revolutions per minute at 5° C. for 10 minutes (Sorvall, SS-34 rotor). The supernatant was injected into a high pressure liquid chromatography apparatus, equipped with a 5 micron RP-8 column (Merck company), and eluted with aqueous alcohol solution.

Results:

At time 0, the indolpyruvate was not present in the plasma, at least within the determination limits of the present method (0,01 gamma/ml). After oral administration, the indolpyruvate reached levels of 0,86±0,21 gamma/ml at 30 minutes, 0,20±0,02 gamma/ml at 60 minutes, 0,53±0,24 gamma/ml at 75 minutes: and finally 0,19±0,04 gamma/ml at 90 minutes.

Determination of Cerebral Levels

Sprague-Dawley rats were also used to determine the effect of the indolpyruvate administered orally in 10 mg/kg doses on cerebral concentrations of indolpyruvate, serotonin and dopamine.

The animals were decapitated 60 minutes after treatment. The cerebral hemispheres were rapidly removed, weighed and homogenized with a double volume of physiological solution plus 0,1 ml of 20% vitamin C.

1 ml of homogenate was treated with 0,43 ml of 12% trichloroacetic acid and 0,025 ml of 20% vitamin C. After standing at 5° C. for 20 minutes, the mixture was centrifuged at 11,000 revolutions per minute (Sorvall centrifuge, SS-34 rotor) for 10 minutes at 5° C. The supernatant was removed and injected into a high pressure liquid chromotography apparatus equipped with a 5 micron RP-8 column (Merck Company) and eluted with aqueous alcohol.

Results:

The indolpyruvate was not present in the brain, at least within the measurements of this method (0,04 gamma/g of tissue). Serotonin ranged from 0,870±0,02 gamma/g of tissue to 1,40±0,03 gamma/g of tissue in the controls. Dopamine showed no substantial modifications.

These pharmacological tests show that oral administration of indolpyruvate leads to an increase in the plasma level of this substance, which decreases over time. As the plasma level decreases with time, the cerebral level of serotonin increases. This shows that the disappearance of indolpyruvate from the plasma results in and increase in serotonin in the brain tissue.

EXAMPLE 3

Determination of Pain Releaving Activity

This was evaluated using the writhing test, with a 3% aqueous acetic acid solution injected intraperitoneally as the pain inducing agent. 3-Indolpyruvic acid was injected in the animals 40 minutes before the acetic acid, in a 10 mg/kg i.p. dose. The experiment was run on 60 male Swiss albino mice, weighing 18–24 g and fasting for three hours the animals were divided into groups of 20 animals: controls treated with 0,9% NaCl; controls treated with formal glycering plus 10% gum arabic in a 1:5 ratio; and animals treated with 3-indolpyruvic acid in a 10% solution in formal glycerin: gum arabic in a 1:5 ratio. After the acetic acid inoculation, the animals were placed in groups of five in plastic cages for mice and observed for a period of 20 minutes. The number of torsions the animals showed in that period was recorded. On the basis of the mean reduction of the number of torsions of the treated animals with respect to the controls, the pain releaving activity of the test compound was calculated. Under these experimental conditions, 3-indolpyruvic acid in 10 mg/kg i.p. doses, after removal of the interference of the blank, showed an approximately 30% inhibition of dolorific activity.

EXAMPLE 4

Potentiation of Sodium Pentobarbital Sleep

The test was run on male Sprague-Dawley rats weighing 220–250G. The sodium pentobarbital used to induce sleep was 30 mg/kg i.p. After administration of the sleep inducing substance the time necessary to induce sleep was measured in minutes, as well as the time in minutes which the animal remained asleep. 3-Indolpyruvic acid was injected in a 10 mg/kg i.p. dose, 40 minutes before the sodium pentobarbital.

The experiment was run on groups of 10 animals each (controls treated with 0,9% NaCl; controls treated with formal glycerin: gum arabic in 1:7 ratio, animals treated with 3-indolpyruvic acid in a 10% solution in formal glycerin: gum arabic in a 1:7 ratio). On the basis of the mean induction times and sleep durations the activity of 3-indolpyruvic acid was calculated. Under these experimental conditons, 3-indolpyruvic acid in 10 mg/kg i.p. doses, after removing the interference of the blank, had no effect on the sleep induction, but prolonged the duration of said sleep by approximately 25%.

EXAMPLE 5

Potentiation of Thiopental Narcosis

The test was run on male albino Swiss mice weighing 20-25 g. The test was based on the administration of a sub-hypnotic dose of thiopental (40 mg/kg i.p.) and on the observation of the eventual appearance and duration of sleep.

3-Indolpyruvic acid was injected in 10 mg/kg i.p. doses 40 minutes before the thiopental. The experiment was run on groups of 10 animals each (controls treated with 9,9 NaCl; controls treated with 10 mg/kg i.p. n-methylglucamine, animals treated with 10 mg/kg i.p. 3-indolpyruvic acid and 10 mg/kg i.p. n-methylglucamine). Under these experimental conditions, 3-indolpyruvic acid induced sleep which lasted for a very long period.

EXAMPLE 6

Spontaneous Motor Activity

Female Swiss albino mice weighing 20-25 g were used. Spontaneous motor activity was observed in individual animals, and was recorded by placing the animal in a Basil activity cage (Mod. 7401) for two hours before and three hours after administration of the test substance. Two groups of 9 animals each were used (controls treated with 20 mg/kg i.p. n-methylglucamine, animals treated with 20 mg/kg n-methylglucamine+20 mg/kg 3-indolpyruvic acid i.p.). In the control animals, in the three hours following administration, a reduction of 65% was observed in motor activity. In the treated animals, this reduction was only 30%. Even through these results are preliminary, they indicate a potentiation of spontaneous motor activity in mice.

EXAMPLE 7

Effect on Brain Serotonin in Hyperammoniemia

A preliminary experiment was conducted on groups of 2 male Sprague-Dawley rats each, weighing 220-250 g. Hyperammoniemia was induced by administration of 5 moles/kg i.p. of ammonium acetate one hour before sacrifice. 3-Indolpyruvic acid was administered in 10 mg/kg p.o. doses one hour before the ammonium acetate, that is 2 hours before sacrifice. After decapitation, the cerebral hemispheres were rapidly removed, weighed and homogenized with a double volume of physiological solution +0,1 ml of 20% vitamin C. 1 ml of homogenate was treated with 0,43 ml of 12% TCA and 0,025 ml of 20% vitamin C. After standing for 5 minutes at 5° C., the mixture was centrifuged at 11,000 revolutions per minute in a Sorvall centrifuge, SS 34 rotor, for 10 minutes at 5° C. The supernatant was removed and injected into a high pressure liquid chromatograph, equipped with a RP-8 column (Merck). Administration of 3-indolpyruvic acid led in one case to a 20% increase, and in the other a 50% increase in brain serotonin.

EXAMPLE 8

Effect on Reserpin-Induced Depletion

Male Sprague-Dawley rats were used weighing 200-240 g. The animals were divided into groups of 4 (controls; treated with reserpin; treated with reserpin+3-indolpyruvic acid). The reserpin was administered in a dose of 1 mg/kg s.c. 3-indolpyruvic acid was administered after various times (4, 7, 18, 24 hours) in 10 mg/kg o.s. doses. Two hours after the adminstration of 3-indolpyruvic acid, the animals were decapitated and, using the method described above, the cerebral levels of noradrenalin, dopamine, 5-hydroxyindolacetic acid (5-HIAA), serotonin (5-HT) and tryptophan (TRP) were determined. The most evident results were obtained after 18 hours: the animals treated with reserpin showed a depletion of noradrenalin, dopamine and 5-HT, and a 30% increase in 5-HIAA. The animals treated with reserpin and 3-indolpyruvic acid showed an equal depletion of noradrenalin, dopamine and 5-HT, turnover of brain serotonin.

EXAMPLE 9

Acute Treatment

Acute treatment was given to 18 male Sprague-Dawley rats weighing 200-240 g, divided in groups of 9 animals. The controls were treated with i.p. N-methylglucamine and 0,9% NaCl; the treated animals however received 3-indolpyruvic acid dissolved in N-methylglucamine+NaCl. One hour after administration, the animals were sacrificed, and the plasma and cerebral levels were determined for tryptophan and its derivatives according to the methods described above. The animals treated with 3-indolpyruvic acid showed a very large reduction in plasma serotonin levels and an approximately 25% increase in plasma tryptophan levels. At the cerebral level, increases were observed in 5-HIAA (11,6%) 5-HT (12,6%) and tryptophan (43%).

PHARMACEUTICAL USE

3-Indolpyruvic acid or its pharmaceutically useful ester or salt thus are shown to be useful in increasing cerebral serotonin levels in mammals, including man, for the treatment of central nervous system disturbances which involve reduced cerebral serotonin levels. Examples of these disturbances include psychic depressions, insomnia, lack of appetite, neuroendocrin imbalances, etc.

The low toxicity of the drug allows it to be used even in relatively high doses. In practice, administration is oral in any of the common pharmaceutical forms which are prepared by means of traditional processes well known in the pharmaceutical field. These forms include doses in solid and liquid form, such as pills, capsules, solutions, syrups and the like.

A non-limiting example of a composition suitable for oral administration in capsule form is given below.

3-indolpyruvic acid
Starch
Lactose
Magnesium stearate
We claim:

1. A pharmaceutical composition to increase brain serotonin levels in mammals comprising an effective amount of 3-indolpyruvic acid or a pharmaceutically acceptable salt thereof, to increase cerebral serotonin levels in mammals.

2. A method for increasing brain serotonin levels in mammals comprising administering orally a therapeutically effective amount of 3-indolpyruvic acid or a pharmaceutically acceptable salt thereof.

3. A method according to claim 2 wherein there is employed 3-indolpyruvic acid.

4. A pharmaceutical composition according to claim 1 wherein there is employed 3-indolpyruvic acid.

* * * * *